United States Patent [19]

Wong et al.

[11] Patent Number: 5,374,541
[45] Date of Patent: Dec. 20, 1994

[54] COMBINED USE OF β-GALACTOSIDASE AND SIALYLTRANSFERASE COUPLED WITH IN SITU REGENERATION OF CMP-SIALIC ACID FOR ONE POT SYNTHESIS OF OLIGOSACCHARIDES

[75] Inventors: Chi-Huey Wong, Rancho Sante Fe; Federico C. A. Gaeta, Olivenhain, both of Calif.

[73] Assignees: The Scripps Research Institute, La Jolla; Cytel Corporation, San Diego, both of Calif.

[21] Appl. No.: 57,526

[22] Filed: May 4, 1993

[51] Int. Cl.$^5$ .................... C12P 19/04; C12P 19/12; C12N 9/10
[52] U.S. Cl. ........................ 435/74; 435/97; 435/101; 435/175; 435/193
[58] Field of Search ............... 435/74, 97, 101, 193, 435/175

[56] References Cited

U.S. PATENT DOCUMENTS

| | | | |
|---|---|---|---|
| 4,918,009 | 4/1990 | Nilsson | 435/73 |
| 5,180,674 | 1/1993 | Roth | 435/97 |
| 5,246,840 | 9/1993 | Nilsson | 435/101 |
| 5,278,299 | 1/1994 | Wong et al. | 536/53 |

OTHER PUBLICATIONS

Ichikawa et al., *J. Am. Chem. Soc.*, 113(12):4698–4700 (1991).
David et al., *Adv. Carbohyd. Chem. Biochem.*, 49:175–237 (1991).

*Primary Examiner*—Herbert J. Lilling
*Attorney, Agent, or Firm*—Welsh & Katz, Ltd.

[57] ABSTRACT

A single reaction vessel process for the synthesis of a sialylated galactoside is disclosed. The synthesis utilizes a β-galactosidase to catalyze the reaction of a galactose-containing substrate and an acceptor to form a new galactosyl glycoside that is then sialylated using a cyclic multienzyme synthesis system to form CMP-sialic acid that sialylates the formed galactosyl glycoside in the presence of an α-sialyltransferase. The value of $K_m/V_{max}$ for the formed galactosyl glycoside as a substrate for the α-sialyltransferase is less than one-third the $K_m/V_{max}$ value for the galactose-containing substrate for that α-sialyltransferase.

11 Claims, 3 Drawing Sheets

Scheme 1

Scheme 2

Scheme 3

COMBINED USE OF β-GALACTOSIDASE AND SIALYLTRANSFERASE COUPLED WITH IN SITU REGENERATION OF CMP-SIALIC ACID FOR ONE POT SYNTHESIS OF OLIGOSACCHARIDES

This invention was made with government support under Contract No. GM 44154 awarded by the National Institutes of Health. The government has certain rights in the invention.

TECHNICAL FIELD

The present invention relates to synthesis of sialylated glycosides, and particularly to the one pot synthesis of such materials using multiple enzymes, including β-galactosidase and sialyltransferase in coupled, cyclic reactions.

BACKGROUND ART

Sialyl-oligosaccharides are of growing importance due to their function as ligands of selectins [(a) Phillips et al., *Science*, 250:1130 (1990); (b) Lowe et al., *Cell*, 63:475 (1990); (c) Lasky, *Science*, 258:964 (1992)] and as important recognition elements on the surface of a variety of cells, [Magnani et al., *Cancer Res.*, 46:5489 (1983)]. Enzymatic approaches to the synthesis of these compounds have proven to be useful, [(a) Ichikawa et al., *Anal. Biochem.*, 202:215 (1992); (b) Toone et al., *Tetrahedron*, 45:5365 (1989); (c) David et al., *Adv. Carbohydr. Chem. Biochem.*, 49:175 (1991)] especially that based on glycosyltransferases coupled with regeneration in situ of sugar nucleotides. Wong et al., *J. Org. Chem.*, 47:5416 (1982); Wong et al., *J. Org. Chem.*, 57:4343 (1992); Auge et al., *Carbohydr. Res.*, 151:147 (1986); Thiem et al., *Angew. Chem. Int. Ed. Engl.*, 30:1164 (1991); Thiem et al., *Synthesis*, 141 (1992); Ichikawa et al., *J. Am. Chem. Soc.*, 113:4768 (1991); Ichikawa et al., *J. Am. Chem. Soc.*, 113:6300 (1991); Ichikawa et al., *J. Am. Chem. Soc.*, 114:9283 (1992). By using galactosyltransferase and sialyltransferase, sialyl N-acetyllactosamine, for example, was obtained in moderate yields. Ichikawa et al., *J. Am. Chem. Soc.*, 113:6300 (1991).

Glycosidases have also been utilized in glycosylation. The yields, however, are relatively low and the regioselectivity is often difficult to control, [(a) Nilsson et al., *TIBTECH;* 6:256 (1988); (b) Kobayashi et al., *J. Am. Chem. Soc.*, 113:3079 (1991); (c) Chaplin et al., *J. Chem. Soc. Perkin Trans.*, 1:235 (1992); (d) Look et al., *Tetrahedron Lett.*, 33:4253 (1992); (e) Sakai et al., *J. Carbohyd. Chem.*, 11:553 (1992); (f) Vanderkerckhove et al., *Glycobiology*, 2:541 (1992); (g) Kitahata et al., *Agric. Biol. Chem.*, 55:2433 (1991)] although certain glycosidases catalyze regioselective transglycosylation. Sakai et al., *J. Carbohyd. Chem.*, 11:553 (1992); Vanderkerckhove et al., *Glycobiology*, 2:541 (1992).

Another problem with the use of glycosidases is that the product of the reaction is subject to the enzymatic cleavage, making the process difficult to control. Thus, the product for the glycosyl transfer reaction is itself a substrate for the enzyme and is cleaved.

For example, Nilsson, *Carbohyd. Res.*, 188:9–17 (1989) reported yields of only about 10–35 percent using a β-galactosidase in a transglycosylation. Some isolated products made by such transglycosylations were also separately sialylated using CMP-Neu5Ac and a α(2,3-)sialyltransferase.

SUMMARY

A process for forming a sialylα(2→3/6)β-galactoside is thus contemplated. That process comprises the steps of:

admixing in a single vessel the following components to form a reaction mixture:
 (i) a catalytic amount of β-galactosidase;
 (ii) a catalytic amount of α(2,3/6)sialyltransferase;
 (iii) a β-galactose-containing donor substrate for the β-galactosidase;
 (iv) an acceptor substrate for the β-galactosidase;
 (v) a sialic acid;
 (vi) a CMP-sialic acid regenerating system comprising at least two moles of phosphoenolpyruvate per each mole of sialic acid, and catalytic amounts of ATP, myokinase, pyruvate kinase, inorganic pyrophosphatase, CMP-sialic acid synthetase and the α(2,3/6)sialyltransferase; and
 (vii) an aqueous buffer solution containing enzymatically sufficient amounts of metal ion cofactors for said enzymes and having a pH value of about 6 to about 8;

and maintaining the reaction mixture at a temperature of about zero degrees C. to about 45° C. for a time period sufficient for a β-galactosyl glycoside formed by the β-galactosidase-catalyzed reaction of the galactose-containing donor substrate and the acceptor substrate to be sialylated. The formed galactosyl glycoside has a $K_m/V_{max}$ value as a substrate for the sialyltransferase that is less than one-third the $K_m/V_{max}$ value of the β-galactose-containing donor substrate for the sialyltransferase.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are, thus, described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Bonding positions of glycosidic linkages are illustrated with an arrow separating the respective ring positions. Each saccharide unit is a pyranose.

Abbreviations
Gal = galactosyl;
GalNAc = N-acetylgalacto;
Glc = glucosyl;
GlcNAc = N-acetylgluco;
Lac = lactose;
LacNAc = N-acetyllactosamine;
Man = Mannose;
ManNAc = N-acetylmannosamine; and
Neu5Ac = sialyl (N-5acetylneuraminyl).

BRIEF DESCRIPTION OF THE DRAWINGS

In the drawings forming a portion of this disclosure.

DETAILED DESCRIPTION OF THE INVENTION

It was envisioned that a sequential formation of two glycosidic bonds using a glycosidase followed by a glycosyltransferase in homogeneous solution in one reaction vessel would provide an oligosaccharide that is no longer a substrate for the glycosidase would overcome a problem associated with the use of a glycosidase for glycosyl transfer.

Using such a process as described hereinafter, one can prepare trisaccharide precursors to cell adhesion ligands such as sialyl Le$^x$ and sialyl Le$^a$, as well as analogs to such precursors. Exemplary trisaccharide precursors are illustrated below as Compounds 5 (sialyl Le$^x$), 6 (sialyl Le$^a$) and 7 (analog). Fucosylation by well known enzymatic or chemical synthesis means, after appropriate blocking, provides the sialylated Lewis ligands and the corresponding analog.

CMP-sialic acid that can react with more of the β-galactosyl glycoside.

Figure 2:
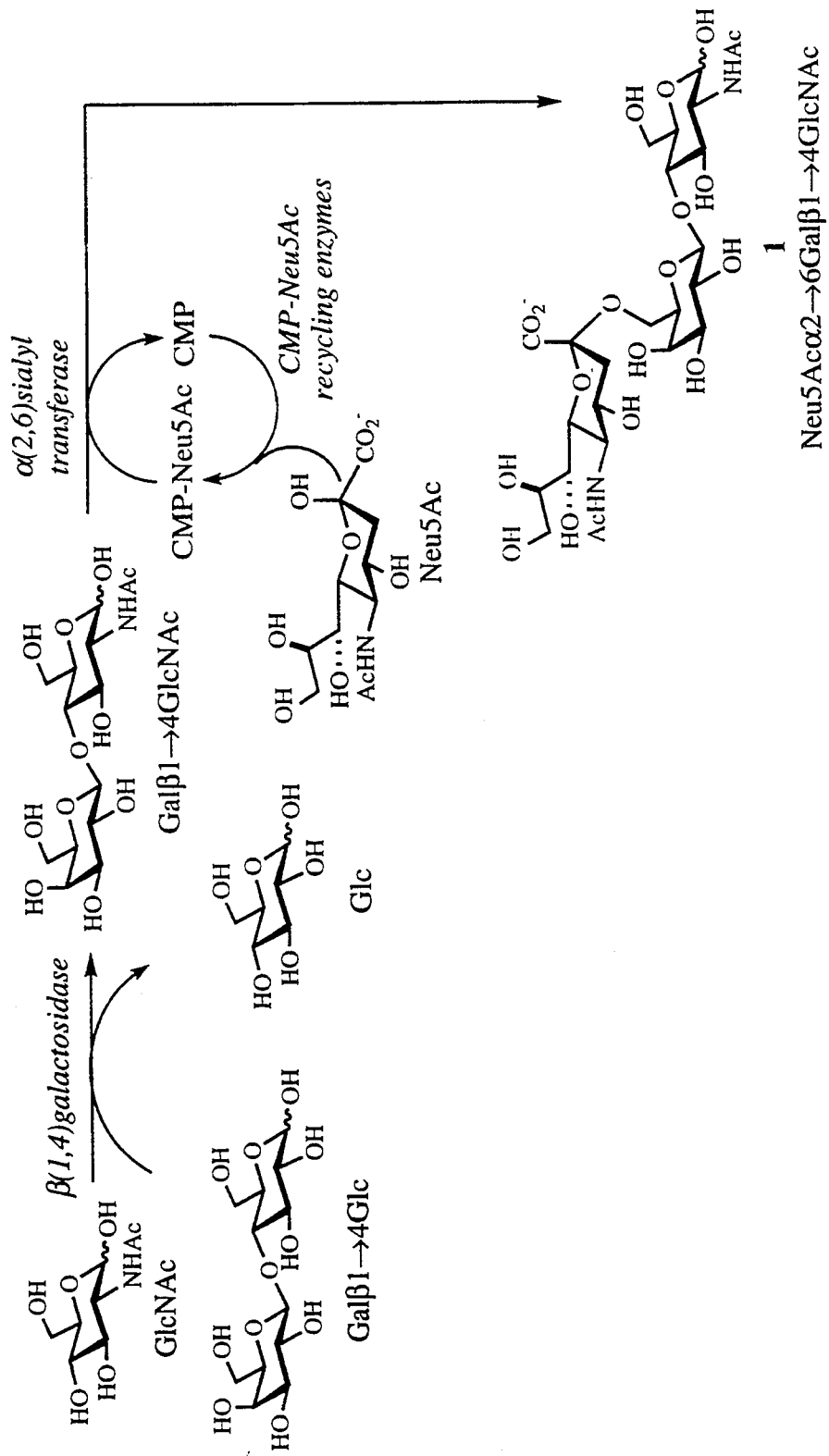
FIG. 2 shows a depiction as Scheme 2 of specifically coupled reactions utilized in the invention.

A specific reaction sequence is illustrated in Scheme 2 (FIG. 2). Fucosylation of Compounds 1 or 2 provides analogs of sialyl Le$^x$ that inhibit intercellular adhesion to cells that contain the ELAM-1 or GMP 140 receptor.

Also illustrated hereinbelow are sialylated Compound 2 that was similarly prepared using GlcNAc-βOallyl instead of the GlcNAc as the acceptor substrate, as well as Compounds 3 and 4 that were prepared via the β(1,4)galactosidase using (5-thioGlc) and (2-N$_3$)Glc in place of GlcNAc as the acceptor substrate. Compound 3 was not sialylated in the reaction, and Compound 4 was sialylated, but poorly.

Scheme 3 (FIG. 3), which follows Scheme 2 (FIG. 2), again utilizes GlcNAcβOallyl (Compound 8) as a galactosyl acceptor to form Galα1→4GlcNAcβOallyl, Compound 9. Compound 9 was then similarly sialylated using α(2,3)sialyltransferase to form Compound 10, Neu5Acα2→3Galβ1→4GlcNAcβOallyl.

The synthesis of LacNAc in Scheme 2 (FIG. 2) cata-

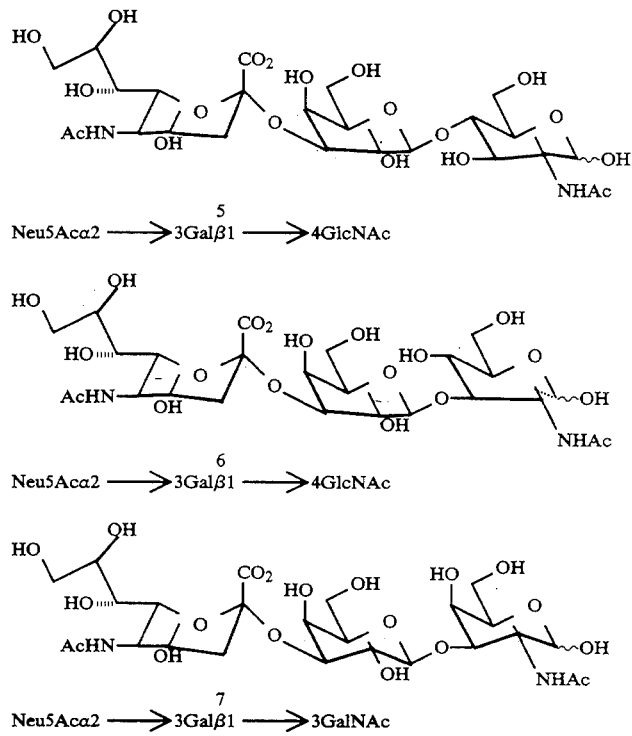

5
Neu5Acα2 ──▶3Galβ1 ──▶4GlcNAc

6
Neu5Acα2 ──▶3Galβ1 ──▶4GlcNAc

7
Neu5Acα2 ──▶3Galβ1 ──▶3GalNAc

Figure 1:
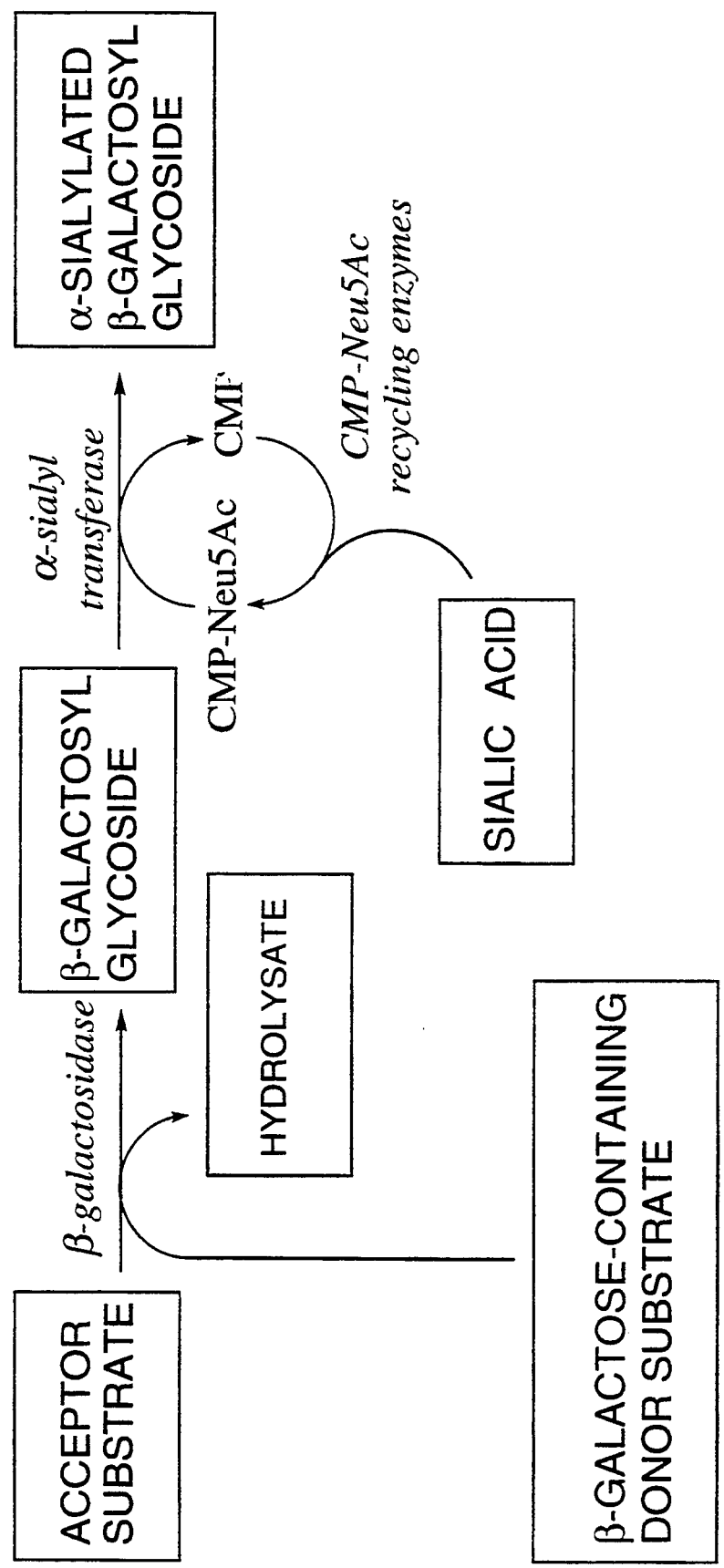
FIG. 1 shows a depiction as Scheme 1 of the coupled reactions utilized in the invention.

The description that follows illustrates that concept through the synthesis of α(2,6)- and α(2,3)sialylgalactosylβglycosides based on a β-galactosidase and α-sialyl-transferase coupled with regeneration in situ of CMP-sialic acid (CMP-Neu5Ac) as is illustrated generally in Scheme 1, (FIG. 1).

Thus, in accordance with the general reaction sequence shown in Scheme 1(FIG. 1), a β-galactose-containing donor substrate and an acceptor substrate are reacted in the presence of the β-galactosidase to form a new β-galactosyl glycoside containing the acceptor. A hydrolysate is also formed by galactosyl bond cleavage of the donor. The β-galactosyl glycoside so formed reacts with a CMP-sialic acid in the presence of the α-sialyl transferase to form the α-sialylated-β-galactosyl glycoside product and CMP. The CMP is recycled using CMP-Neu5Ac recycling enzymes to reform lyzed by the β-galactosidase (0.02 cents/unit) starts with inexpensive lactose and GlcNAc, and the process does not require the expensive β(1,4)-galactosyltransferase ($13/unit). Although the βgalactosidase reaction is reversible, the formed LacNAc is irreversibly sialylated with the sialyltransferase, because the sialylated saccharide is no longer a substrate for the β-galactosidase as is LacNAc. Fucosylation of Compound 10 of Scheme 3 (FIG. 3) provides a sialyl Lewis X analog that inhibits intercellular binding by cells such as activated endothelial cells that contain the ELAM 1 receptor and cells that express sialyl Lewis X such as neutrophils.

B. The Process

A process contemplated is carried out in a single reaction vessel and such a process is often referred to in the art as a "one pot" process. As such, all of the reagents, including the enzymes, and starting chemicals are admixed together at substantially the same time and in a single reaction medium.

A process for forming a sialyl$\alpha(2\rightarrow 3/6)\beta$-galactoside is thus contemplated. That process comprises the steps of:

admixing in a single vessel the following components to form a reaction mixture:
(i) a catalytic amount of $\beta$-galactosidase;
(ii) a catalytic amount of $\alpha(2,3/6)$sialyltransferase;
(iii) a $\beta$-galactose-containing donor substrate for the $\beta$-galactosidase;
(iv) an acceptor substrate for the $\beta$-galactosidase;
(v) a sialic acid;
(vi) a CMP-sialic acid regenerating system comprising at least two moles of phosphoenolpyruvate per each mole of sialic acid, and .catalytic amounts of ATP, myokinase, pyruvate kinase, inorganic pyrophosphatase, CMP-sialic acid synthetase; and
(vii) an aqueous buffer solution containing enzymatically sufficient amounts of metal ion cofactors for said enzymes and having a pH value of about 6 to about 8;
and maintaining the reaction mixture at a temperature of about zero degrees C. to about 45° C. for a time period sufficient for a $\beta$-galactosyl glycoside formed by the $\beta$-galactosidase-catalyzed reaction of the galactose-containing donor substrate and said acceptor substrate to be sialylated. The formed galactosyl glycoside has a $K_m/V_{max}$ value as a substrate for the sialyltransferase that is less than one-third the $K_m/V_{max}$ value of the $\beta$-galactose-containing donor substrate for the sialyltransferase.

$K_m$ is the Michaelis constant in units of moles/liter. $V_{max}$ is the reaction velocity at a constant concentration of enzyme, and is in units of enzyme units/milligram, one enzyme unit being that amount of enzyme that will catalyze the transformation of one micromole of substrate per minute under optimal conditions. The value of $K_m/V_{max}$ is the slope of the line obtained from a Lineweaver-Burk plot.

An $\alpha$-sialyltransferase is one of the three principal enzymes utilized herein. This enzyme transfers sialic acid to Gal with the formation of an $\alpha$-linkage between the two saccharides. Bonding (linkage) between the saccharides is between the 2-position of Neu5Ac and the 3- or 6-position of Gal. The $\alpha$-sialyltransferase is therefore sometimes referred to generally as an $\alpha(2,3/6\text{-})$sialyltransferase or a galactosyl $\alpha(2,3/6)$sialyltransferase to indicate that either type of enzyme can be used and the moiety to which the sialyl group is transferred.

An exemplary $\alpha$-sialyltransferase is referred to as $\alpha(2,3)$sialyltransferase (EC 2.4.99.6) and transfers sialic acid to the Gal of a Gal$\beta 1\rightarrow 3$GlcNAc or Gal$\beta 1\rightarrow 4$GlcNAc glycoside [Wen et al., *J. Biol. Chem.*, 267:21011 (1992)]. This enzyme is thought to be responsible for sialylations of asparagine-linked oligosaccharides in glycoproteins, and can be isolated from rat liver. [Weinstein et al., *J. Biol. Chem.*, 257:13845 (1982).] Another exemplary $\alpha$-2,3-dialyltransferase (EC 2.4.99.4) transfers sialic acid to the Gal of a Gal$\beta 1\rightarrow 3$GalNAc glycoside [Gillespie et al., *J. Biol. Chem.*, 267:21004 (1992)]. This enzyme is thought to be responsible for sialylation of serine- or threonine-linked oligosaccharides in glycoproteins, and can be isolated from porcine submaxillary glands. [Rearick et al., *J. Biol. Chem.*, 254:4444 (1979).]

An enzyme originally isolated from bovine colostrum that is used illustratively here and referred to $\alpha(2,6\text{-})$sialyltransferase (EC 2.4.99.1) transfers sialic acid to the 6-position of a Gal$\beta 1\rightarrow 4$GlcNAc (LacNAc) [Beyer et al., *Adv. Enzymol.*, 52:23-175 (1981)]. An enzyme having similar specificity and slightly different $K_m$ and $V_{max}$ values was isolated also from rat liver by Weinstein et al., supra.

CMP-Sialic acid synthetase is an enzyme that is utilized in the CMP-sialic acid regenerating system that is discussed in detail hereinafter. For example, CMP-sialic acid synthetase can be isolated and purified from cells and tissues containing the synthetase enzyme by procedures well known in the art. See, e.g., Gross et al., *Eur. J. Biochem.*, 168:595 (1987); Vijay et al., *J. Biol. Chem.*, 250(1):164 (1975); Zapata et al., *J. Biol. Chem.*, 264(25):14769 (1989) and Higa et al., *J. Biol. Chem.*, 260(15):8838 (1985). The gene for this enzyme has also been sequenced. Vann et al., *J. Biol. Chem.*, 262:17556 (1987). Shames et al. also recently reported overexpression of the gene for use in a gram scale synthesis of CMP-Neu5Ac. *Glycobiology*, 1:187 (1991). This enzyme is also commercially available.

A contemplated $\beta$-galactosidase cleaves a $\beta$-bonded Gal unit from the non-reducing terminus of a galactoside and is capable of forming a new $\beta(1\rightarrow 3)$- or $\beta(1\rightarrow 4)$- or $\beta(1\rightarrow 6)$ galactoside. Formation of a $\beta(1\rightarrow 3)$-$\beta(1\rightarrow 4)$ bond is preferred, and a preferred enzyme is often referred to as a $\beta(1\rightarrow 3/4)$galactosidase.

An exemplary $\beta(1\rightarrow 4)$galactosidase is that produced by *Bacillus circulans* (EC 3.2.1.23) [Sakai et al., *J. Carbohyd. Chem.*, 11:553 (1992)]. This enzyme utilized illustratively herein cleaves the glycosidyl bond in lactose, and in the presence of GlcNAc can be used to form Gal$\beta(1\rightarrow 4)$GlcNAc (LacNAc). This $\beta$-galactosidase is particularly preferred because of its high regioselectivity in the formation of a $\beta(1\rightarrow 4)$ bond.

Another exemplary $\beta$-galactosidase is the $\beta(1\rightarrow 3)$galactosidase from bovine testes. This enzyme can provide high regioselectivity for $\beta(1\rightarrow 3)$ bond formation using GlcNAc$\beta$-OMe as the acceptor [Nilsson, *Carbohydr. Res.*, 188:9-17 (1989)].

The $\beta$-galactosidase of *E. coli* almost exclusively forms Gal$\beta(1\rightarrow 6)$GlcNAc. Use of this enzyme is therefore not preferred herein.

A $\beta$-galactose-containing donor substrate for the $\beta$-galactosidase is one of the reactants used herein. This material contains a galactosyl saccharide unit $\beta$-bonded to a leaving group such as another saccharide such as glucose as is used here illustratively, or a p-nitrophenyl group.

One of the particular advantages of the present process is that it can utilize relatively inexpensive precursors such as lactose and $\beta$-galactosidase to prepare a more costly $\beta$-galactosyl galactoside such as LacNAc, here, that itself is sialylated to form the product. Thus, lactose is a particularly preferred galactose-containing donor substrate.

An acceptor substrate for the $\beta$-galactosidase is another reactant of this process. This acceptor is also a substrate for the $\beta$-galactosidase when used for transglycosylation but not glycolysis, and therefore must contain a hydroxyl group at the 3-, 4- or 6-position appropriate to the $\beta$-galactosidase utilized, as does the GalNAc used illustratively herein.

A salient point in the use of this process is that the value of $K_m/V_{max}$ for the $\beta$-galactosyl glycoside formed by the $\beta$-galactoside reaction on the $\beta$-galactose-containing donor and acceptor substrates be less than one-third, preferably less than about one-tenth, more preferably less than about one-fiftieth, and most preferably less than about one-hundredth, that of the $K_m/V_{max}$ value of the β-galactose-containing donor for the sialylation reaction catalyzed by the α-sialyltransferase. Thus, because both the β-galactose-containing donor substrate and formed galactosyl glycoside are present in the same vessel at the same time, and the former is usually present at a higher concentration, that former donor substrate could be sialylated in preference to its reaction product. Selection of appropriate donor and acceptor substrates and their concentrations, coupled with selection of an appropriate α-sialylating enzyme help to assure that the desired sialylated product is prepared.

Values for $K_m$ and $V_{max}$ for several galactosyl glycosides are available in the published literature and can be obtained using well known enzymatic techniques. Exemplary values for several donor/galactosyl glycosides are listed below in Table 1 whose data are taken from Beyer et al., Adv. Enzymol., 52:23–175 (1981) and Weinstein et al., J. Biol. Chem., 257:13845 (1982), wherein both types of galactosides are referred to as "acceptors" for the α-sialyltransferase.

Galβ1→3GlcNAc and then NeuAcα2→3Galβ1→3GalNAc (Compound 6).

Lactose and GlcNAc can also be used as donor and acceptor with either of the above-mentioned βgalactosidase enzymes and α(2,3)sialyltransferase (EC 2.4.99.6) that exhibits a preference for sialylation of a substrate containing the Galβ1→3/4GlcNAc group. Thus, use of the B. circulans β-galactosidase with lactose, GlcNAc and EC 2.4.99.6 provides NeuAcα2→3Galβ1→4GlcNAc (Compound 5).

It is to be understood that a useful galactose-containing substrate for a particular β-galactosidase may not be bound by the α-sialyltransferase or be bound very poorly, and if bound may not be sialylated or be sialylated very slowly. The $K_m/V_{max}$ values for that compound and the formed glycosyl glycoside can indicate an almost infinite difference.

Sialic acid (Neu5Ac, and sometimes also abbreviated AcNeu, NeuAc or NANA) is also required. As noted previously, the use of sialic acid to regenerate the sialyl donor of Scheme 1 (FIG. 1) drives the trans-sialidase-catalyzed equilibrium reaction toward making the desired sialylated product.

A contemplated sialic acid includes not only sialic acid itself (5-N-acetylamino-3,5-dideoxy-D-glycero-D-

TABLE 1

$K_m$ and $V_{max}$ Values for Acceptor Molecules and α-Sialyltransferases

| α-( )Sialyl transferase[1] | Acceptor | $K_m$ (mM) | $V_{max}$ (units/mg) | $K_m/V_{max}$ mM − units / mg |
|---|---|---|---|---|
| 2,6 | Galβ1→4GlcNAc | 12 | 1 | 12 |
| EC 2.4.99.1 | Galβ1→6GlcNAc | 140 | 0.03 | 4667 |
|  | Galβ1→4Glc | 390 | 1.02 | 382 |
| 2,6 | Galβ1→4GlcNAc | 1.62 | 0.93 | 1.74 |
| Rat liver | Galβ1→4Glc | 129 | 0.30 | 430 |
|  | Galβ1→3GlcNAc[3,4] | — | — | >100 |
|  | Galβ1→3GalNAc[3,5] | — | — | very large |
| 2,3 | Galβ1→3GalNAc | 0.21 | 8.9 | 0.024 |
| EC 2.4.99.4 | Galβ1→3GlcNAc | 65 | 4.4 | 15 |
|  | Galβ1→4GlcNAc | 42 | 0.11 | 382 |
|  | Galβ1→6GlcNAc | 29 | 0.24 | 121 |
|  | Galβ1→4Glc | 180 | 0.62 | 290 |
|  | lacto-N-tetraose[2] | 27 | 3.6 | 7.5 |
| 2,3 | Galβ1→3GalNAc[3] | — | — | >10 |
| EC 2.4.99.6 | Galβ1→4GlcNAc | 2.7 | 0.75 | 3.6 |
|  | Galβ1→4Glc | 9.4 | 0.91 | 10 |
|  | lacto-N-tetraose[2] | 0.09 | 1.00 | 0.09 |
|  | Galβ1→3GlcNAc | 0.64 | 1.16 | 0.55 |

[1]Parenthesized numbers indicating the positions of bond formation are shown below as 2,6 and 2,3 for the enzymes.
[2]Lacto-N-tetraose = Galβ1→3GlcNAcβ1→3Galβ1→4Glc.
[3]Value approximated from the data in Weinstein et al., J. Biol. Chem., 257:13845 (1982).
[4]This acceptor was a poor substrate for the enzyme and formed slightly more product than did Galβ1→4Glc, indicating either or both of a large $K_m$ and a very small $V_{max}$, so that the value of $K_m/V_{max}$ is approximated to be greater than 100 as a conservative value.
[5]No sialylated product was reported to be formed, so the value of $K_m/V_{max}$ is a very large number.

With the data above or similar data in mind, one can see that the exemplary use of lactose (Galβ1→4Glc) as donor with Galβ1→4GlcNAc and α(2,6)sialyltransferase (EC 2.4.99.1) provides reactants and intermediate galactosyl glycoside having values of $K_m/V_{max}$ that differ by a factor of greater than about 30. Similarly, readily available lacto-N-tetraose as donor can be used with GalNAc as acceptor, bovine testes β-galactosidase and α(2,3)sialyltransferase (EC 2.4.99.4) to form Galβ1→3GalNAc as the galactosyl glycoside that is sialylated to form Neu5Acεα2→3GalβGalNAc (Compound 7). Lactose can similarly be used as donor with bovine testes β-galactosidase and GlcNAc as acceptor with α(2,3)sialyltransferase (2.4.99.4) to form galacto-2-nonulosonic acid; Neu5Ac), but also 9-substituted sialic acids such as a 9-0-$C_1$-$C_6$ acyl-Neu5Ac like 9-0-lactyl-Neu5Ac or 9-0-acetyl-Neu5Ac, 9-deoxy-9-fluoro-Neu5Ac and 9-azido-9-deoxy-Neu5Ac. Use of sialic acid analogs having changes at other positions impairs the activity of one or more of the enzymes utilized herein. The synthesis and use of these compounds in a silylation procedure is disclosed in international application WO 92/16640, published Oct. 1, 1992.

Figure 3:
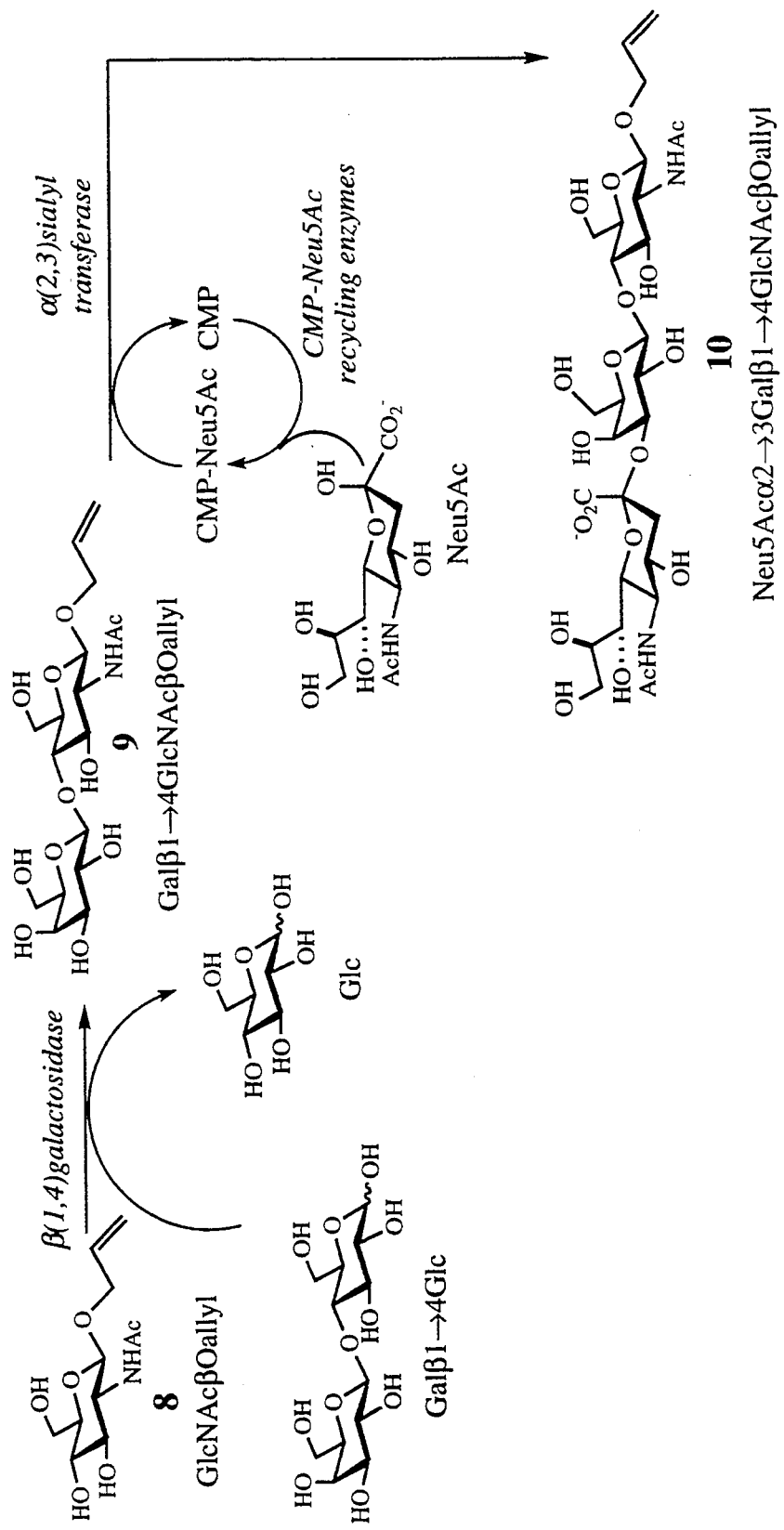
FIG. 3 shows a depiction as Scheme 3 of other specifically coupled reactions utilized in the invention.

The CMP-sialic acid recycling system utilizes CMP-sialic acid synthetase as noted previously. As shown in Scheme 2 (FIG. 2), CMP-sialic acid (shown in the scheme as CMP-Neu5Ac) reacts with the formed galactosyl glycoside (shown in the scheme as Galβ1→4GlcNAc) in the presence of α(2,6)sialyltransferase (shown in the scheme as α(2,6)sialyltransferase) to form the sialylated product. It is this reformation and use of CMP-sialic acid that drives the conversion of the galactosyl glycoside toward complete formation of the desired sialylated product, e.g., Compound 1. A similar CMP-sialic acid recycling system is shown in Scheme 3 (FIG. 3).

The CMP-sialic acid regenerating system used in the present process comprises cytidine monophosphate (CMP), a nucleoside triphosphate, a phosphate donor, a kinase capable of transferring phosphate from the phosphate donor to nucleoside diphosphates and a nucleoside monophosphate kinase capable of transferring the terminal phosphate from a nucleoside triphosphate to CMP.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system of the present invention are used to catalyze the phosphorylation of CMP. NMK's are commercially available (Sigma Chem. Co., St. Louis, Mo; Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated galactosyl glycoside. Preferred phosphate donors are phosphoenolpyruvate (PEP) and acetyl phosphate. A particularly preferred phosphate donor is PEP.

The selection of a particular kinase for use in accordance with the present invention depends upon the phosphate donor employed. When acetyl phosphate is used as the phosphate donor, the kinase is acetyl kinase. When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the stoichiometric substrates (e.g. free Neu5Ac and PEP) is consumed.

Thus, in the sialylation example, CMP is converted to CDP, whose conversion is catalyzed by nucleoside monophosphate kinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the galactosyl glycoside, the released CMP re-enters the regenerating system to reform CDP, CTP and CMP-sialic acid. The formed PPi is scavenged as discussed below, and forms inorganic phosphate (Pi) as a byproduct. Pyruvate is also a byproduct.

The byproduct pyruvate can also be made use of in another reaction in which N-acetylmannosamine (ManNAc) and pyruvate are reacted in the presence of NeuAc aldolase (EC 4.1.3.3) to form sialic acid. Thus, the sialic acid can be replaced by ManNAc and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase coupled with inorganic pyrophosphatase (PPase)-catalyzed decomposition of the released inorganic pyrophosphate. This enzymatic synthesis of sialic acid and its 9-substituted derivatives and the use of a resulting sialic acid in a different sialylating reaction scheme is disclosed in International application WO 92/16640, published on Oct. 1, 1992.

As used herein, the term "pyrophosphate scavenger" refers to substances that serve to remove inorganic pyrophosphate from a reaction mixture of the present invention. Inorganic pyrophosphate (PPi) is a byproduct of the preparation of CMP-Neu5Ac.

Produced PPi can feed back to inhibit other enzymes such that glycosylation is reduced. However, PPi can be degraded enzymatically or by physical means such as sequestration by a PPi binding substance. Preferably, PPi is removed by hydrolysis using inorganic pyrophosphatase (PPase; EC 3.6.1.1), a commercially available PPi catabolic enzyme (Sigma Chem. Co., St. Louis, Mo.; Boehringer Mannheim, Indianapolis, Ind.), and that or a similar enzyme serves as the pyrophosphate scavenger.

Use of the CMP-sialic acid regenerating system provides at least two advantages over the use of preformed CMP-sialic acid. First, CMP-sialic acid is an expensive reagent that is relatively difficult to prepare. Second, CMP-sialic acid has a half-life in aqueous buffers as are used here of only a few hours. As a consequence, large quantities of that reagent are required to be used, and even then, the CMP-sialic acid often has to be added to the reaction mixture more than one time during the reaction.

A before-mentioned α(2,3/6)sialyltransferase can also be formally included in the CMP-sialic acid recycling system. However, as that enzyme has already been discussed, it is not included here.

The concentrations or amounts of the various reactants used in this process depend upon numerous factors including reaction conditions such as temperature and pH value, and the choice and amount of donor or acceptor saccharides. However, so long as the donor concentration is not so great that the difference in $K_m/V_{max}$ values is not swamped by the donor concentration, the relative amounts of donor and acceptor do not appear to be critical. The larger the difference in $K_m/V_{max}$ values for the donor and galactosyl glycoside as to the α-sialyltransferase, the greater can be the concentration of the donor substrate.

Because this process permits regeneration of activating nucleotides, activated donor Neu5Ac and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, acceptor saccharide and enzymes are selected such that the process proceeds until the sialic acid is consumed.

By way of example, when the concentration of a sialic acid is about 20 mM, preferred concentrations of the other non-enzyme reactants are about 250 mM for the β-galactose-containing donor substrate, about 600 mM for the acceptor substrate, about 2 mM for CMP, about 0.2 mM for the nucleoside triphosphate (ATP) and about 40 mM for the phosphate donor (PEP). Thus, the ratio of the concentration of the three saccharides (sialic acid:donor substrate:acceptor substrate) acceptor is about 20:250:600. The CMP is present at about one-tenth amount of the sialic acid, and ATP is present at about one-tenth the amount of CMP. The phosphate donor is present at at least about twice the concentration of the sialic acid. So long as the phosphate donor is present at at least twice the concentration of the sialic acid, the sialic acid provides the stoichiometric limitation. Otherwise, the relative concentrations do not appear critical, as discussed before. Where the sialic acid is prepared in situ from an N-acetylmannosamine, as discussed before, the relative amount of the sialic acid can be based on the N-acetylmannosamine utilized.

Each of the enzymes is present in a catalytic amount. As used herein, the phrase "catalytic amount" means that amount of an enzyme at least sufficient to catalyze, in a non-rate limiting manner, the conversion of that enzyme's substrate to product.

The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

It is to be remembered that the CMP and CTP as well as the sialic acid and CMP-sialic acid are recycled in a contemplated process. As a consequence of that fact, one may start a reaction with either or both of CMP and CTP, as well as with either or both of sialic acid and CMP-sialic acid, as well as an N-acetylmannosamine and NeuAc aldolase, as discussed before.

Thus, the above ratio is for the total concentration of these materials. The choice of which to use is mostly a question of cost and availability, with the least expensive, most available reagent typically being the reagent of choice. Inasmuch as CMP and sialic acid are the least expensive and most readily available of those pairs, those reagents are used to start the reaction, with the amount discussed before being those for the total amount of each pair used.

The above ingredients are combined by admixture in a buffered aqueous solution (reaction medium). That buffered medium has a pH value of about 6 to about 8. The buffer is devoid of chelators that bind enzyme cofactors such as $Mg^{+2}$ or $Mn^{+2}$, which are present as needed by particular enzymes. The selection of a buffer is based on the ability of the buffer to maintain pH value at the desired level. Where the pH value is about 7.5, a preferred buffer is HEPES.

The buffered aqueous solution or reaction medium utilized is preferably free of detergents or other organic solubilizing agents such as ethanol or methanol. In addition, the enzymes, particularly the β-galactosidase and α-sialyltransferase, are preferably utilized in free form and not linked to a support such as a polymer, so that the reaction medium is substantially homogeneous, at least initially, as some precipitates can form during the reaction.

The temperature at which an above process is carried out can range from just above freezing to the temperature at which the most sensitive enzyme denatures. That temperature range is preferably about zero degrees C. to about 45° C., and more preferably at about 20° C. to about 30° C.

The reaction mixture so formed is maintained for a period of time sufficient for the β-galactosyl glycoside to be formed by the β-galactosidase-catalyzed reaction of the β-galactose-containing donor substrate and the acceptor substrate. Some of that product can often be detached after a few hours, with recoverable amounts usually being obtained within 24 hours. It is preferred to optimize the yield of the process, and the maintenance time is usually about 36 to about 120 hours.

The produced α-sialyl β-galactosyl glycoside can be used without purification. However, it is usually preferred to recover the product. Standard, well known techniques for recovery of sialylated saccharides such as thin or thick layer chromatography or ion exchange chromatography can be used. It is preferred to use one or more column chromatographic techniques for the recovery as is discussed hereinafter and in the literature cited herein.

Results

A representative synthesis of Neu5Acα(2,6)-LacNAc (Compound 1) is discussed below. To a 1.07 mL HEPES buffer (0.2M, 20 mM $MgCl_2$, 5.3 mM $MnCl_2$, 20 mM KCl, pH 7.5) containing 12.3 mg Neu5Ac (20 mM; provided by Dr. U. Kragl, Research Center, Jülich, Germany), 180 mg Lac (250 mM), 265 mg GlcNAc (600 mM), 30.2 mg PEP (trisodium salt, 40 mM), CMP (2 mM) and ATP (0.2 mM) were added myokinase (MK, EC 2.7.4.3; 6 U), pyruvate kinase (PK, EC 2.7.1.40; 80 U), inorganic pyrophosphatase (PPase, EC 3.6.1.1; 4 U), CMP-Neu5Ac synthetase (EC 2.7.43; 0.32 U), α(2,6)sialyltransferase (EC 2.4.99.1; 0,052 U) and 1 mg of crude β-galactosidase (EC 3.2.1.23) from *Bacillus Circulans* (provided by Daiwa Kasei KK, Osaka, Japan). The total volume was adjusted to 2 mL.

The reaction was conducted for 91 hours under argon at room temperature and monitored by TLC on silica gel 60 ($R_f$: Lac, 0.16; LacNAc, 0.27; Gal, 0.29; Glc, 0.37; β(2,6)sialyl-LacNAc, 0.45; Neu5Ac, 0.54; GlcNAc, 0.54 in 7:2:1 (v/v/v) iPrOH/$H_2O$/$NH_4OH$).

The reaction mixture was centrifuged and the supernatant was directly applied to a BioGel P2 Column (200–400 mesh, 43×2 cm) with water as the eluent. The trisaccharide-containing fractions were pooled and lyophilized to give 6.8 mg of Compound 1: Neu5Acα(2,6-)Galβ(1,4)GlcNAc (26 percent yield).

The ¹H NMR spectrum was identical to that reported. [Ichikawa et al., *J. Am. Chem. Soc.*, 113:4768 (1991).] No other sialylated product could be detected.

Neither Lac, one of the starting materials, nor Galβ1→6GlcNAc, a by-product of the β-galactosidase reaction [Sakai et al., *J. Carbohydr. Chem.*, 11:553 (1992)] is a substrate for α(2,6)sialyltransferase [for detailed kinetic study of α(2,6)sialyltransferase, see Paulson et al., *J. Biol. Chem.*, 252:2363 (1977); Galβ1→4GlcNAc: $V_{max}$=1.00, $K_m$=12 mM; Galβ1→6GlcNAc: $V_{max}$=0.03, $K_m$=140 mM; Galβ1→4Glc: $V_{max}$=1.02, $K_m$=390 mM] due to the high $K_m$ (390 mM and low $V_{max}$ (3 percent), values, respectively. Put differently, the value of $K_m/V_{max}$ for the β-galactosyl glycoside used here [Galβ1→4GlcNAc] of 12 mM, is less than one-tenth that of the $K_m/V_{max}$ values for the other two possible β-galactosyl glycoside [Galβ1→6GlcNAc and Galβ1→4Glc] of about 4667 mM and 390 mM, respectively.

Of several galactosides studied, lactose was found to be the best substrate for the *B. circulans* β-galactosidase. That β-galactosidase accepts the following substrates with the indicated, parenthesized relative rates: Lac (100), o-nitrophenyl β-galactoside (10.6), methyl β-galactoside (1).

In a similar manner, the sialylated saccharide (Compound 2) was also prepared. Compounds 3 and 4 were prepared separately in about 20 percent yield with the galactosidase; however, Compound 3 was not a substrate for the sialyltransferase, and Compound 4 was a very weak substrate. Compound 10 was prepared as follows.

The pH value of a solution of allyl 2-acetamido-2-deoxy-β-D-glucopyranoside (26 mg, 100 μmol), lactose (34 mg, 100 μmol), N-acetylneuraminic acid (31 mg, 100 μmol), phospho(enol)pyruvate trisodium salt (48.6 mg, 200 μmol), CMP (3.2 mg, 10 μmol), ATP (5.5 mg, 10 μmol), MgCl₂·6H₂O (16.3 mg, 80 μmol; 20 mM), MnCl₂·4H₂O (4.0 mg, 20 μmol; 5mM), KCl (6.9 mg, 80 μmol; 20 mM), and DTT (0.12 mg, 0.8 μmol; 0.2 mM) in HEPES buffer (200 mM, 4 mL) was adjusted by M NaOH to 7.5. To the solution were added the following enzymes: pyruvate kinase (EC 2.7.1.40; 500 U), nucleoside monophosphate kinase (EC 2.7.4.4; 5 U), inorganic pyrophosphatase (EC 3.6.1.1; 10 U), β-galactosidase (EC 3.2.1.23; from *Bacillus circulans;* 1.0 mg), CMP-Neu5Ac synthetase (EC 2.7.743; 0.3 U), and α2,3sialyltransferase (EC 2.4.99.6; 1 U), and the reaction mixture was gently stirred at room temperature under an argon atmosphere for two days and resulted in a yield of Compound 10 of about 10–15 percent. The product was isolated in a similar manner described in Ichikawa et al., *J. Am. Chem. Soc.*, 114:9283 (1992).

In summary, a new efficient procedure for the synthesis of a sialyl-trisaccharide has been shown. The synthesis employed a β-galactosidase and a sialyltransferase, and each enzyme worked sequentially and selectively, in one-pot, to form a sialyl N-acetyllactosamine. Although the glycosidase catalyzes the reversible reaction (i.e., glycosidic bond-hydrolyzing and -forming reactions), a combined usage of these two enzymes in one pot allows the synthesis of sialyl trisaccharides in an irreversible manner. In addition, regeneration of CMP-Neu5Ac from CMP catalyzed by the two kinases and CMP-Neu5Ac synthetase in the sialylation reaction reduces the cost of the process and the problem of product inhibition caused by CMP.

Analytical Data

¹H NMR Neu5Acα(2→6)Galβ(1→4)GlcNAc (Compound 1): δ1.677 (1H, t, J=12.5 Hz, H-3ax of Neu5Ac), 1.985 (3H, s, NHAc of GlcNAc), 2.022 (3H, s, NHAc of Neu5Ac), 2.628 (1H, dd, J-5 Hz, 12.5 Hz, H-3eq of Neu5Ac), 4.409 (1H, d, J=8 Hz, H-1 of Gal), 4.780 (0.5H, d, J=9 Hz, H-1b of GlcNAc), 5.154 (0.5H, d, J=2.5 Hz, H-1a of GlcNAc).

¹H NMR Neu5Acα(2→6)Galβ(1→4) GlcNAc-βOAllyl (Compound 2): δ1.672 (1H, t, J=12.5 Hz, H-3ax of Neu5Ac), 1.984 (3H, s, NHAc of GlcNAc), 2.015 (3H, s, NHAc of Neu5Ac), 2.623 (1H, m, J=4.5, 12.25 Hz, H-3eq of Neu5Ac), 4.130 (1H, m, allyl), 4.294 (1H, m, allyl), 4.403 (1H, d, J=8 Hz, H-1 of Gal), 4.569 (0.5H, d, J=8.5 Hz, H-1 b of GlcNAc), 5.221 (1H, m, allyl), 5.268 (1H, m, allyl), 5.872 (1H, m, allyl); $R_f$ 0.50 in 7:2:1 (v/v/v) iPrOH/H₂O/NH₄OH.

1H NMR spectrum of Galβ1→4(5-thio)Glc (Compound 3) was identical with that reported previously: Gautheron-Le Narvor et al., *J. Chem. Soc., Chem. Commun.*, 1130 (1991).

¹H NMR Galβ1→4(2-N₃)Glc (Compound 4): δ3.27 (dd, J=8.32, 9.82 Hz, H-2b), 4.42 (dd, J=7.75 Hz, H-1'b), 4.69 (d, J=8.72 Hz, H-1b), 5.31 (d, J=3.50 Hz, H-1a). The ¹H NMR spectrum of Compound 4 was in good agreement with that of allyl glycoside derivative of Compound 4 [Ichikawa et al., *J. Am. Chem. Soc.*, 114:9283 (1982)].

The foregoing is intended as illustrative of the present invention but not limiting. Numerous variations and modifications may be effected without departing from the true spirit and scope of the novel concepts of the invention.

We claim:

1. A process for forming an α-sialylated galactosyl glycoside that comprises the steps of:
   admixing in a single vessel the following components to form a reaction mixture:
   (i) a catalytic amount of β-galactosidase;
   (ii) a catalytic amount of α(2,6)- or α(2,3)sialyltransferase;
   (iii) a β-galactose-containing donor substrate for said β-galactosidase;
   (iv) an acceptor substrate for said β-galactosidase;
   (v) a sialic acid;
   (vi) a CMP-sialic acid regenerating system comprising at least two moles of phosphoenolpyruvate per each mole of said sialic acid, and catalytic amounts of ATP, myokinase, pyruvate kinase, inorganic pyrophosphatase and CMP-sialic acid synthetase; and
   (vii) an aqueous buffer solution containing enzymatically sufficient amounts of metal ion cofactors for said enzymes and having a pH value of about 6 to about 8;
   and maintaining said reaction mixture at a temperature of about zero degrees C. to about 45° C. for a time period sufficient for a β-galactosyl glycoside formed by the β-galactosidase-catalyzed reaction of said galactose-containing donor substrate and said acceptor substrate to be sialylated, said galactosyl glycoside having a $K_m/V_{max}$ value as a substrate for said sialyltransferase that is less than one-third the $K_m/V_{max}$ value of said galactose-containing donor substrate for said sialyltransferase.

2. The process according to claim 1 including the further step of recovering said formed sialylated galactosyl glycoside.

3. The process according to claim 1 wherein said sialylated galactosyl glycoside is NeuSAcα2→6Galβ1→4GlcNAc or NeuSAcα2-6Galβ1→4GlcNAc-Oallyl.

4. The process according to claim 1 wherein said galactose-containing donor substrate (iii) is lactose.

5. The process according to claim 1 wherein said acceptor substrate for said β-galactosidase is GlcNAc.

6. The process according to claim 1 wherein said β-galactosidase is the β(1,4)galactosidase of *Bacillus circulans*.

7. The process according to claim 1 wherein said sialyltransferase is α(2,6)sialyltransferase.

8. The process according to claim 1 wherein said sialyltransferase is α(2,3)sialyltransferase.

9. The process according to claim 1 wherein said galactosyl glycoside has a $K_m/V_{max}$ value as a substrate for said sialyltransferase that is less than one-tenth the $K_m/V_{max}$ value of said galactose-containing donor substrate for said sialyltransferase.

10. A process for forming an β-sialylated galactosyl glycoside that comprises the steps of:
   admixing in a single vessel the following components to form a reaction mixture:
   (i) a catalytic amount of *Bacillus circulans*β(1,4)-galactosidase;
   (ii) a catalytic amount of α(2,3)sialyltransferase or α(2,6)sialyltransferase;
   (iii) lactose as a donor substrate for said β(1,4)-galactosidase;
   (iv) N-acetylglucosamine or allyl N-acetylglucosamine glycoside as an acceptor substrate for said β(1,4)-galactosidase;
   (v) sialic acid;
   (vi) a CMP-sialic acid regenerating system comprising at least two moles of phosphoenolpyruvate per each mole of said sialic acid, and catalytic amounts of ATP, myokinase, pyruvate kinase, inorganic pyrophosphatase and CMP-sialic acid synthetase; and
   (vii) an aqueous buffer solution containing enzymatically sufficient amounts of metal ion cofactors for said enzymes and having a pH value of about 6 to about 8;
   and maintaining said reaction mixture at a temperature of about zero degrees C. to about 45° C. for a time period sufficient for N-acetyllactosamine or allyl N-acetyllactosamine glycoside formed by the β-galactosidase-catalyzed reaction of said donor substrate and said acceptor substrate to be sialylated to form an α-sialylated galactosyl glycoside.

11. The process according to claim 10 including the further step of recovering said formed sialylated galactosyl glycoside.

* * * * *